US010961205B2

(12) United States Patent
Sasikumar et al.

(10) Patent No.: US 10,961,205 B2
(45) Date of Patent: *Mar. 30, 2021

(54) 1,2,4-OXADIAZOLE DERIVATIVES AS IMMUNOMODULATORS

(71) Applicants: Pottayil Govindan Nair Sasikumar, Bangalore (IN); Muralidhara Ramachandra, Bangalore (IN); Seetharamaiah Setty Sudarshan Naremaddepalli, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/806,872

(22) Filed: Mar. 2, 2020

(65) Prior Publication Data

US 2020/0199086 A1 Jun. 25, 2020

Related U.S. Application Data

(63) Continuation of application No. 16/192,030, filed on Nov. 15, 2018, now Pat. No. 10,590,093, which is a continuation of application No. 15/713,671, filed on Sep. 24, 2017, now Pat. No. 10,173,989, which is a continuation of application No. 15/298,539, filed on Oct. 20, 2016, now Pat. No. 9,771,338, which is a continuation of application No. 14/478,759, filed on Sep. 5, 2014, now abandoned.

(30) Foreign Application Priority Data

Sep. 6, 2013 (IN) .......................... 4011/CHE/2013

(51) Int. Cl.
| | | |
|---|---|---|
| *C07D 271/06* | (2006.01) | |
| *A61K 31/4245* | (2006.01) | |
| *C07D 273/08* | (2006.01) | |
| *A61K 31/433* | (2006.01) | |
| *A61K 45/06* | (2006.01) | |
| *A61K 31/395* | (2006.01) | |
| *C07D 273/00* | (2006.01) | |

(52) U.S. Cl.
CPC .......... *C07D 271/06* (2013.01); *A61K 31/395* (2013.01); *A61K 31/4245* (2013.01); *A61K 31/433* (2013.01); *A61K 45/06* (2013.01); *C07D 273/00* (2013.01); *C07D 273/08* (2013.01); *Y02A 50/30* (2018.01)

(58) Field of Classification Search
CPC .......................... A61K 31/4245; C07D 271/06
See application file for complete search history.

(56) References Cited

U.S. PATENT DOCUMENTS

| | | | |
|---|---|---|---|
| 3,227,725 A | 1/1966 | Fernand et al. | |
| 5,387,585 A | 2/1995 | Borer et al. | |
| 5,665,718 A | 9/1997 | Godel et al. | |
| 8,735,553 B1 | 5/2014 | Li et al. | |
| 9,771,338 B2 * | 9/2017 | Sasikumar ............ | A61K 45/06 |
| 10,173,989 B2 | 1/2019 | Sasikumar et al. | |
| 10,590,093 B2 * | 3/2020 | Sasikumar .......... | A61K 31/395 |
| 2005/0272779 A1 | 12/2005 | Edwards et al. | |
| 2007/0197522 A1 | 8/2007 | Edwards et al. | |
| 2007/0225332 A1 | 9/2007 | Gu et al. | |

(Continued)

FOREIGN PATENT DOCUMENTS

| | | |
|---|---|---|
| WO | 2001014557 A1 | 3/2001 |
| WO | 2002079499 A1 | 10/2002 |

(Continued)

OTHER PUBLICATIONS

Harvey RD. Immunologic and Clinical Effects of Targeting PD-1 in Lung Cancer, Clinical Pharmacology & Therapeutics (2014) 96 (02) : 214-223.
Pedoeem, et al. Programmed death-1 pathway in cancer and autoimmunity, Clinical Immunology (2014) 153:145-152.
Shi et al. The role of PD-1 and PD-L1 in T-cell immune suppression in patients with hematological malignancies. Journal of Hematology & Oncology 2013, 6:74 p. 1-6.
Jin et al. Role of PD-1 in Regulating T-Cell Immunity. Current Topics in Microbiology and Immunology (2010) published online: Sep. 11, 2010 350: pp. 17-37.

(Continued)

*Primary Examiner* — Matthew P Coughlin
(74) *Attorney, Agent, or Firm* — Benjamin Aaron Adler

(57) ABSTRACT

The present invention relates to methods of modulating an immune response mediated by a PD-1 signaling pathway and of treating a cancer or an infectious disease. A subject is administered a compound(s) or a pharmaceutically acceptable salt or pharmaceutically acceptable composition thereof of formula (I)

In the ring Q is S or O. $R_1$ substituents are an optionally substituted side chain of the amino acid Ser or Thr and $R_3$ substituents are a side chain of the amino acids Asn, Asp, Gln, or Glu. $R_2$ is hydrogen or —CO-Aaa and Aaa is Thr or Ser with a free, amidated or esterified C-terminus. $R_4$ and $R_5$ are independently hydrogen or absent. $R_6$ is hydrogen, alkyl or acyl.

48 Claims, 4 Drawing Sheets

(56) References Cited

U.S. PATENT DOCUMENTS

| | | | |
|---|---|---|---|
| 2009/0099227 | A1 | 4/2009 | Fyfe et al. |
| 2011/0275673 | A1 | 11/2011 | Xiang et al. |
| 2013/0022629 | A1 | 1/2013 | Sharpe et al. |
| 2014/0199334 | A1 | 7/2014 | Sasikumar et al. |
| 2014/0235620 | A1 | 8/2014 | Caferro et al. |
| 2015/0073042 | A1 | 3/2015 | Sasikumar et al. |
| 2020/0061030 | A1 | 2/2020 | Sasikumar et al. |

FOREIGN PATENT DOCUMENTS

| | | | |
|---|---|---|---|
| WO | 2002086083 | A2 | 10/2002 |
| WO | 2003042402 | A2 | 5/2003 |
| WO | 03070711 | A1 | 8/2003 |
| WO | 2004004771 | A1 | 1/2004 |
| WO | 2004056875 | A1 | 7/2004 |
| WO | 2005056550 | A2 | 6/2005 |
| WO | 2006121168 | A1 | 11/2006 |
| WO | 2006133216 | A2 | 12/2006 |
| WO | 2007075749 | A2 | 7/2007 |
| WO | 2008011557 | A2 | 1/2008 |
| WO | 2008039431 | A2 | 4/2008 |
| WO | 2008156712 | A1 | 12/2008 |
| WO | 2009006555 | A2 | 1/2009 |
| WO | 2009059162 | A1 | 5/2009 |
| WO | 2009105712 | A1 | 8/2009 |
| WO | 2010051447 | A1 | 5/2010 |
| WO | 2010077634 | A1 | 7/2010 |
| WO | 2011066389 | A1 | 6/2011 |
| WO | 2011082400 | A2 | 7/2011 |
| WO | 2011137587 | A1 | 11/2011 |
| WO | 2011161699 | A2 | 12/2011 |
| WO | 2012129564 | A2 | 9/2012 |
| WO | 2012168944 | A1 | 12/2012 |
| WO | 2013132317 | A1 | 9/2013 |
| WO | 2013144704 | A1 | 10/2013 |
| WO | 2014055897 | A2 | 4/2014 |
| WO | 2014059173 | A2 | 4/2014 |
| WO | 2014100079 | A1 | 6/2014 |
| WO | 2014110298 | A1 | 7/2014 |
| WO | 2014141104 | A1 | 9/2014 |
| WO | 2014147586 | A1 | 9/2014 |
| WO | 2015033299 | A1 | 3/2015 |
| WO | 2015033301 | A1 | 3/2015 |
| WO | 2016073470 | A1 | 5/2016 |
| WO | 2016142833 | A1 | 9/2016 |
| WO | 2016142852 | A1 | 9/2016 |
| WO | 2016142886 | A2 | 9/2016 |
| WO | 2018047143 | A1 | 3/2018 |

OTHER PUBLICATIONS

Anderson et al., "Lag-3, Tim-3, and TIGIT: Co-inhibitory Receptors with Specialized Functions in Immune Regulation," Immunity, 44(5): 989-1004 (2016).
Ardestani et al., "Cell death features induced in Leishmania major by 1,3,4-thiadiazole derivatives," Exp Parasitol, 132(2): 116-122 (2012).
Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., "Pharmaceutical Solids: A Strategic Approach to Regulatory Considerations," Pharmaceutical Research, 12(7):945-954 (1995).
CAS Registry No. 1252104-30-5 (2013).
CAS Registry No. 1356744-17-6 (2012).
CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Database Registry Chemical Abstracts, STN Accession No. 172410-37-6.
Database Registry Chemical Abstracts, STN Accession No. 197083-27-5.
Extended European Search Report for EP Application No. 16761169.8 dated Jul. 2, 2019 (Our reference CUH-40480).
Extended European Search Report for EP Application No. 16761184 dated Jun. 26, 2018 (Our reference CUH-40201).
Extended European Search Report for European Application No. 18162983.3 dated Jun. 27, 2018 [our reference CUH-40597].
Graham, "Clinical Trials of HIV Vaccines," HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., "Design of oxobenzimidazoles and oxindoles as novel androgen receptor antagonists," Bioorg Med Chem Letts 22(7):2572-2578 (2012).
International Preliminary Report on Patentability for International Application No. PCT/IB2018/058526 dated May 14, 2020 (Our Reference CUH-41825).
International Search Report and Written Opinion for International Application No. PCT/CN2017/104485 dated Jun. 29, 2018[our reference CUH-42125].
International Search Report and Written Opinion for International Application No. PCT/IB2014/064279 dated Dec. 12, 2014 (our reference CUH-405.25).
International Search Report and Written Opinion for International Application No. PCT/IB2016/051266 dated Jul. 8, 2016 (our reference CUH-404.25).
International Search Report and Written Opinion for International Application No. PCT/IB2016/051343 dated Jul. 28, 2016 (our reference CUH-402.25).
International Search Report and Written Opinion for International Application No. PCT/IB2017/056462 dated Jan. 10, 2018 (our reference CUH-417.25).
International Search Report Written Opinion for International Application No. PCT/US2018/053052 dated Jan. 29, 2019 (our reference CUH-42126).
Lazorchak et al., "Abstract A36: CA-170, an oral small molecule PD-L1 and VISTA immune checkpoint antagonist, promotes T cell immune activation and inhibits tumor growth in pre-clinical models of cancer," Cancer Immunology Research, 5(S3):A36 (2017).
Liu et al., "Immune-checkpoint proteins VISTA and PD-1 nonredundantly regulate murine T-cell responses," PNAS, 112(21): 6682-6687 (2015).
Luo et al., "Principles of Cancer Therapy: Oncogene and Non-oncogene Addiction," Cell, 136(5): 823-837 (2009).
Marechal et al., "1,2,4-oxadiazoles identified by virtual screening and their non-covalent inhibition of the human 20S proteasome," Curr Med Chem 20(18):2351-2362 (2013).
Moussebois et al., "Synthese de Deux Nouveaux Acides Amines Phenoliques Comportant un Cycle 1,2,4-Oxadiazole," Helv. Chim. ACTA, 60(1):237-242 (1977).
Ozcan et al., "Oxadiazole-Isopropylamieds as Potent and Noncovalent Proteasome Inhibitors," J. Med. Chem., 56(10):3783-3805 (2013).
Palazzo et al., "1,2,4-Oxadiazoles—IV. Synthesis and Pharmacological Properties of a Series of Substituted Aminoalkyl- 1,2,4-Oxadiazoles," J. Med. Chem., 351-367 (1961).

(56) References Cited

OTHER PUBLICATIONS

Patwardhan et al., "Structure-Activity Relationship Studies and in Vivo Activity of Guanidine-Based Sphingosine Kinase Inhibitors: Discovery of SphK1- and SphK2—Selective Inhibitors," J. Med. Chem., 58(4):1879-1899 (2015).
Sureshbabu et al., "Synthesis of 1,2,4-oxadiazole-linked Orthogonally Urethane-Protected Dipeptide Mimetics," Tetrahedron Letters, 49(35): 5133-5136 (2008).
Waldmann, "Effective Cancer Therapy Through Immunomodulation," T Annu Rev Med, 57: 65-81 (2006).

\* cited by examiner

1,2,4-OXADIAZOLE DERIVATIVES AS IMMUNOMODULATORS

CROSS-REFERENCE TO RELATED APPLICATIONS

This application is a continuation under 35 U.S.C. § 120 of pending application U.S. Ser. No. 16/192,030, filed Nov. 15, 2018, which is a continuation under 35 U.S.C. § 120 of application U.S. Ser. No. 15/713,671, filed Sep. 24, 2017, now U.S. Pat. No. 10,173,989, which is a continuation under 35 U.S.C. § 120 of U.S. Ser. No. 15/298,539, filed Oct. 20, 2016, now U.S. Pat. No. 9,771,338, which is a continuation under 35 U.S.C. § 120 of application U.S. Ser. No. 14/478,759, filed Sep. 5, 2014, now abandoned, which claims benefit of priority of Indian provisional application number 4011/CHE/2013, filed on Sep. 6, 2013, now abandoned, and for which a certified copy thereof is found in the file wrapper of U.S. Ser. No. 15/298,539, the entirety of all of which are hereby incorporated by reference.

BACKGROUND OF THE INVENTION

Technical Field of the Invention

The present invention relates to 1,2,4-oxadiazole and 1,2,4-thiadiazole compounds and their derivatives therapeutically useful as immune modulators. The invention also relates to pharmaceutical compositions comprising the said 1,2,4-oxadiazole and 1,2,4-thiadiazole compounds and their derivatives as therapeutic agents.

Description of the Related Art

Programmed cell death-1 (PD-1) is a member of the CD28 superfamily that delivers negative signals upon interaction with its two ligands, PD-L1 or PD-L2. PD-1 and its ligands are broadly expressed and exert a wider range of immunoregulatory roles in T cells activation and tolerance compared with other CD28 members. PD-1 and its ligands are involved in attenuating infectious immunity and tumor immunity, and facilitating chronic infection and tumor progression. The biological significance of PD-1 and its ligand suggests the therapeutic potential of manipulation of PD-1 pathway against various human diseases (Ariel Pedoeem et al., Curr Top Microbiol Immunol. (2011); 350:17-37).

T-cell activation and dysfunction relies on direct and modulated receptors. Based on their functional outcome, co-signaling molecules can be divided as co-stimulators and co-inhibitors, which positively and negatively control the priming, growth, differentiation and functional maturation of a T-cell response (Li Shi, et al., Journal of Hematology & Oncology 2013, 6:74).

Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of on-going clinical trials (R D Harvey, Clinical Pharmacology & Therapeutics (2014); 96 2, 214-223).

Programmed death-1 (PD-1) is a co-receptor that is expressed predominantly by T cells. The binding of PD-1 to its ligands, PD-L1 or PD-L2, is vital for the physiological regulation of the immune system. A major functional role of the PD-1 signaling pathway is the inhibition of self-reactive T cells, which serve to protect against autoimmune diseases. Elimination of the PD-1 pathway can therefore result in the breakdown of immune tolerance that can ultimately lead to the development of pathogenic autoimmunity. Conversely, tumor cells can at times co-opt the PD-1 pathway to escape from immunosurveillance mechanisms. Therefore, blockade of the PD-1 pathway has become an attractive target in cancer therapy. Current approaches include six agents that are either PD-1 and PD-L1 targeted neutralizing antibodies or fusion proteins. More than forty clinical trials are underway to better define the role of PD-1 blockade in variety of tumor types (Hyun-Tak Jin et al., Clinical Immunology (Amsterdam, Netherlands) (2014), 153(1), 145-152).

International applications WO 01/14557, WO 02/079499, WO 2002/086083, WO 03/042402, WO 2004/004771, WO 2004/056875, WO2006121168, WO2008156712, WO2010077634, WO2011066389, WO2014055897, WO2014059173, WO2014100079 and U.S. Pat. No. 08,735,553 report PD-1 or PD-L1 inhibitory antibodies or fusion proteins.

Further, International applications, WO2011161699, WO2012/168944, WO2013144704 and WO2013132317 report peptides or peptidomimetic compounds which are capable of suppressing and/or inhibiting the programmed cell death 1 (PD1) signaling pathway.

Still there is a need for more potent, better and/or selective immune modulators of PD-1 pathway. The present invention provides 1,2,4-oxadiazole and 1,2,4-thiadiazole compounds which are capable of suppressing and/or inhibiting the programmed cell death 1 (PD1) signaling pathway.

SUMMARY OF THE INVENTION

In accordance with the present invention, 1,2,4-oxadiazole and 1,2,4-thiadiazole compounds or a pharmaceutically acceptable salt or a stereoisomer thereof, provided which are capable of suppressing and/or inhibiting the programmed cell death 1 (PD1) signaling pathway.

In one aspect, the present invention provides 1,2,4-oxadiazole and 1,2,4-thiadiazole compounds of formula (I):

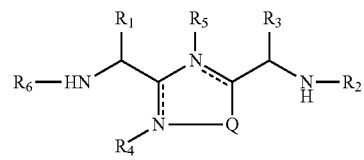

wherein,
Q is S or O;
$R_1$ is a side chain of amino acid Ser or Thr, optionally substituted with alkyl or acyl;
$R_2$ is hydrogen or —CO-Aaa;
Aaa is an amino acid residue Thr or Ser; wherein a C-terminus thereof is a free terminus, is amidated or is esterified;
$R_3$ is a side chain of amino acid Asn, Asp, Gln or Glu;
----- is an optional bond;
$R_4$ and $R_5$ independently are hydrogen or absent;
$R_6$ is hydrogen, alkyl or acyl;
or a pharmaceutically acceptable salt or a stereoisomer thereof.

In a further aspect of the present invention, there is provided a pharmaceutical composition comprising a compound of formula (I) or a pharmaceutically acceptable salt or a stereoisomer and processes for preparing thereof.

In yet another aspect of the present invention, there is provided methods for suppressing and/or inhibiting the programmed cell death 1 (PD1) signaling pathway in a subject by administering 1,2,4-oxadiazole and 1,2,4-thiadiazole compounds of formula (I) or a pharmaceutically acceptable salt or a stereoisomer thereof or pharmaceutical compositions thereof.

In yet another aspect of the present invention, there is provided methods for inhibiting growth of tumour cells and/or metastasis in a subject by administering 1,2,4-oxadiazole and 1,2,4-thiadiazole compounds of formula (I) or a pharmaceutically acceptable salt or a stereoisomer thereof or pharmaceutical compositions thereof.

In yet another aspect of the present invention, there is provided methods for treating an infectious disease or a bacterial, viral and fungal infections in a subject by administering 1,2,4-oxadiazole and 1,2,4-thiadiazole compounds of formula (I) or a pharmaceutically acceptable salt or a stereoisomer thereof or pharmaceutical compositions thereof.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
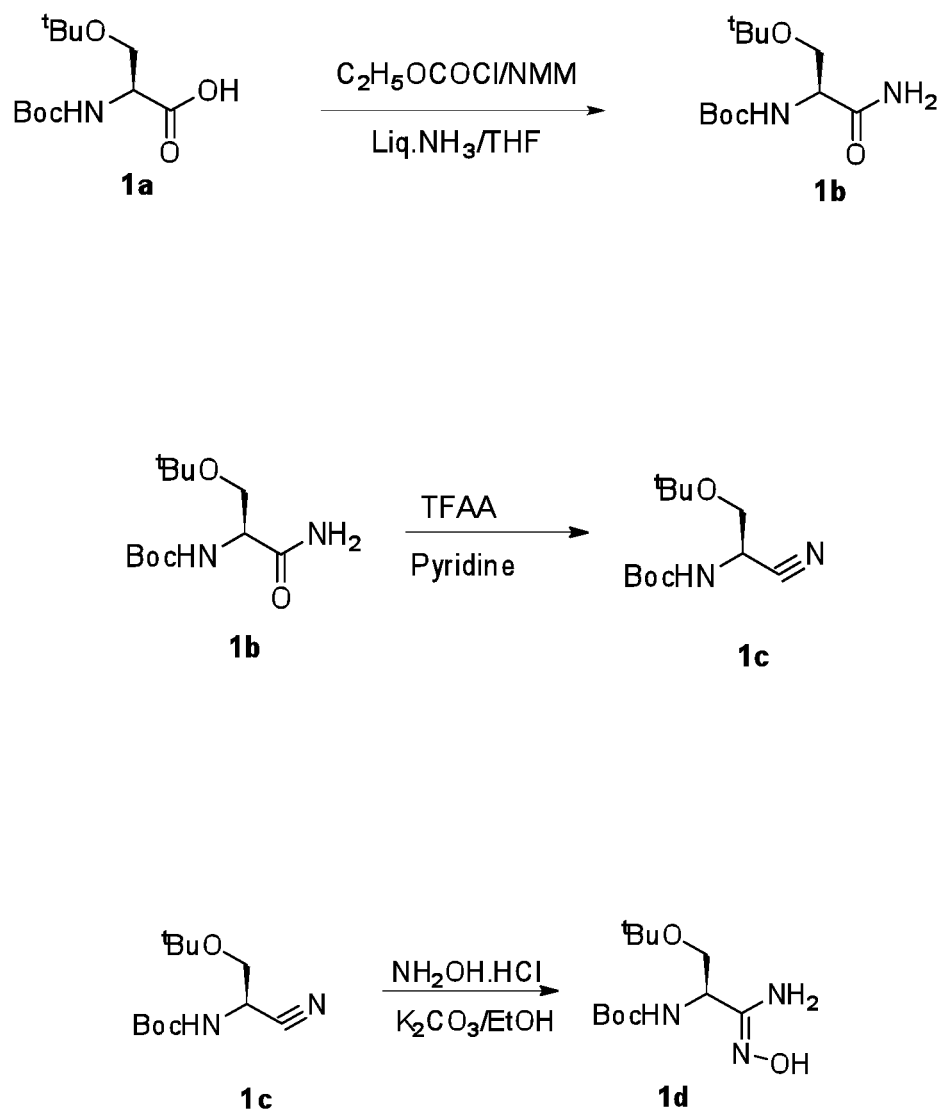
FIGS. 1A-1B depict the chemical synthetic scheme for Compound 1.
Figure 1B:
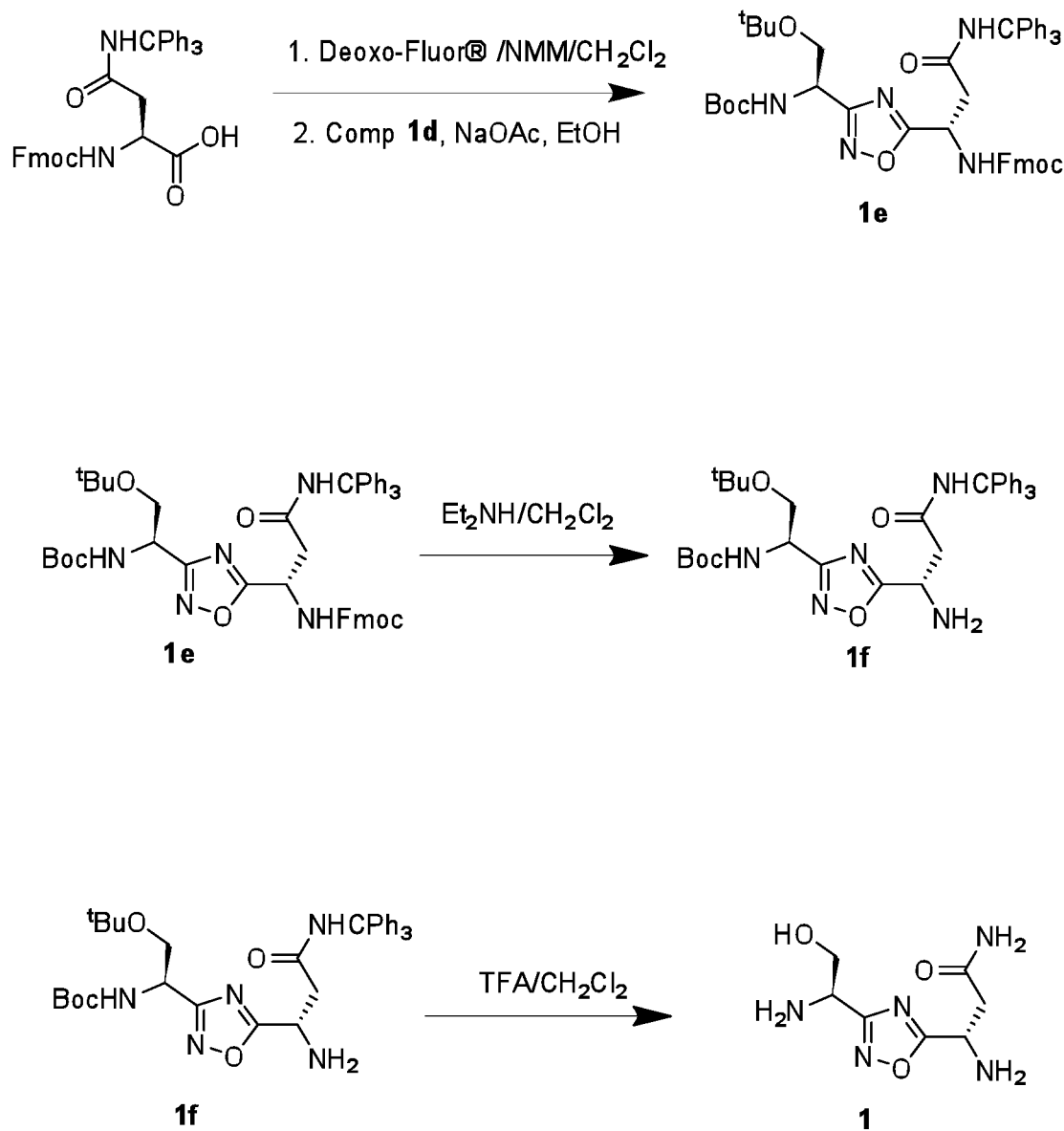

The present invention provides 1,2,4-oxadiazole and 1,2,4-thiadiazole compounds as therapeutic agents useful in methods for treating disorders via immunopotentiation comprising inhibition of immunosuppressive signal induced due to PD-1, PD-L1, or PD-L2 and therapies using them.

Each embodiment is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In one embodiment, the present invention relates to compounds of formula (I)

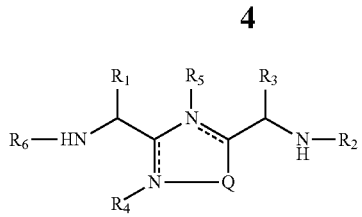

wherein,
Q is S or O;
$R_1$ is a side chain of amino acid Ser or Thr, optionally substituted with alkyl or acyl;
$R_2$ is hydrogen or —CO-Aaa;
Aaa is an amino acid residue Thr or Ser; a C-terminus thereof is a free terminus, is amidated or is esterified;
$R_3$ is side chain of amino acid Asn, Asp, Gln, or Glu;
----- is an optional bond;
$R_4$ and $R_5$ independently are hydrogen or absent;
$R_6$ is hydrogen, alkyl or acyl;
or a pharmaceutically acceptable salt or a stereoisomer thereof.

In another embodiment, the present invention provides compounds of formula (IA)

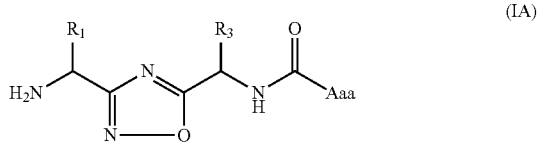

or a pharmaceutically acceptable salt or a stereoisomer thereof; wherein,
$R_1$, $R_3$ and Aaa are as defined in formula (I).

In yet another further embodiment, the present invention provides compounds of formula (IB)

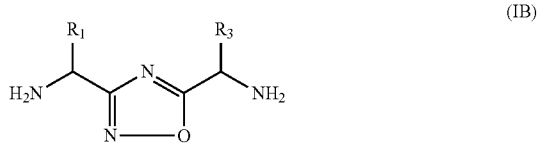

or a pharmaceutically acceptable salt or a stereoisomer thereof; wherein,
$R_1$ and $R_3$ are the same as defined in formula (I).

In yet another further embodiment, for the compound according to formula (I) Q is S.

In yet another further embodiment, for the compound according to formula (I) $R_4$ is hydrogen.

In yet another further embodiment, for the compound according to formula (I) $R_5$ is hydrogen.

The embodiments below are illustrative of the present invention and are not intended to limit the claims to the specific embodiments exemplified.

According to one embodiment, specifically provided are compounds of the formula (I), (IA) and (IB) in which $R_1$ is a side chain of Ser.

According to another embodiment, specifically provided are compounds of the formula (I), (IA) and (IB) in which $R_1$ is a side chain of Thr.

According to yet another embodiment, specifically provided are compounds of the formula (I) in which $R_2$ is hydrogen.

According to yet another embodiment, specifically provided are compounds of the formula (I) in which $R_2$ is —CO-Aaa.

According to yet another embodiment, specifically provided are compounds of the formula (I) and (IA) in which Aaa is Thr.

According to yet another embodiment, specifically provided are compounds of the formula (I) and (IA) in which Aaa is Ser.

According to yet another embodiment, specifically provided are compounds of the formula (I), (IA) and (IB) in which $R_3$ is a side chain of Asn.

According to yet another embodiment, specifically provided are compounds of the formula (I) and (IA) in which $R_3$ is a side chain of Asp.

According to yet another embodiment, specifically provided are compounds of the formula (I) and (IA) in which $R_3$ is a side chain of Gln.

According to yet another embodiment, specifically provided are compounds of the formula (I) and (IA) in which $R_3$ is side a chain of Glu.

According to yet another embodiment, specifically provided are compounds of the formula (I) in which $R_1$ is a side chain of Ser or Thr; $R_2$ is —CO-Aaa; Aaa is an amino acid residue Thr or Ser; wherein C-terminus is free; and $R_3$ is a side chain of Asn or Glu.

According to yet another embodiment, specifically provided are compounds of the formula (I) in which Q is O.

According to yet another embodiment, specifically provided are compounds of the formula (I) in which $R_1$ is a side chain of Ser, optionally substituted with $C_{1-5}$ alkyl such as methyl.

According to yet another embodiment, specifically provided are compounds of the formula (I) in which $R_6$ is hydrogen.

According to yet another embodiment, specifically provided are compounds of the formula (I) in which $R_6$ is acyl such as butyryl.

According to yet another embodiment, specifically provided are compounds of the formula (I) in which $R_4$ and $R_5$ are absent.

According to yet another embodiment, specifically provided are compounds of the formula (I) in which C-terminus of Aaa is free (e.g. —CO$_2$H form).

According to yet another embodiment, specifically provided are compounds of the formula (I) in which C-terminus of Aaa is esterified (e.g. —CO$_2$Me form).

According to yet another embodiment, specifically provided are compounds of the formula (I) in which C-terminus of Aaa is amidated (e.g. —CONH$_2$ form).

According to yet another embodiment, specifically provided are compounds of the formula (I), (IA) and (IB) in which one, more or all amino acid/s is/are D amino acid/s.

In an embodiment, specific compounds of formula (I) without any limitation are enumerated in Table 1 or a pharmaceutically acceptable salt or a stereoisomer thereof.

TABLE 1

| Compound No. | Structure |
| --- | --- |
| 1 | (structure) |
| 2 | (structure) |
| 3 | (structure) |
| 4 | (structure) |
| 5 | (structure) |
| 6 | (structure) |
| 7 | (structure) |

TABLE 1-continued

| Compound No. | Structure |
|---|---|
| 8 | (chemical structure) |
| 9 | (chemical structure) |
| 10 | (chemical structure) |
| 11 | (chemical structure) |
| 12 | (chemical structure) |
| 13 | (chemical structure) |
| 14 | (chemical structure) |
| 15 | (chemical structure) |
| 16 | (chemical structure) |
| 17 | (chemical structure) |
| 18 | (chemical structure) |
| 19 | (chemical structure) |
| 20 | (chemical structure) |
| 21 | (chemical structure) |

TABLE 1-continued

| Compound No. | Structure |
|---|---|
| 22 | [chemical structure] |
| 23 | [chemical structure] |
| 24 | [chemical structure] |
| 25 | [chemical structure] |

In one embodiment, the present invention provides a pharmaceutical composition comprising the compound as disclosed, and a pharmaceutically acceptable carrier or diluent.

In another embodiment, the pharmaceutical composition further comprising at least one of an anticancer agent, chemotherapy agent, or antiproliferative compound.

The compounds as disclosed in the present invention are formulated for pharmaceutical administration.

In one embodiment, the present invention provides use of the compounds as disclosed in the present invention for the preparation of a medicament.

In another embodiment, the present invention provides use of the compounds as disclosed in the present invention for the preparation of a medicament for the treatment of cancer or infectious disease.

In one embodiment, the present invention provides use of the compounds as disclosed in the present invention for the preparation of a medicament for the treatment of bacterial, viral and fungal infections.

In one embodiment, the present invention provides a method of treatment of cancer, wherein the method comprises administration of an effective amount of the compound of the present invention or of a pharmaceutical composition thereof to the subject in need thereof.

In another embodiment the present invention provides a method of modulating an immune response mediated by PD-1 signaling pathway in a subject, comprising administering to the subject a therapeutically effective amount of the compound of the present invention or a pharmaceutical composition thereof such that the immune response in the subject is modulated.

In yet another embodiment the present invention provides a method of inhibiting growth of tumour cells and/or metastasis in a subject, comprising administering to the subject a therapeutically effective amount of compound of the present invention or a pharmaceutical composition thereof capable of inhibiting the programmed cell death 1 (PD1) signaling pathway.

The said tumour cells include cancer such as, but not limited to, bone cancer, cancer of the head or neck, pancreatic cancer, skin cancer, cutaneous or intraocular malignant endometrium, carcinoma of the cervix, carcinoma of the vagina, carcinoma of the vulva, Hogkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia acute lymphoblastic leukemia, chronic lymphocytic leukemia, solid tumours of childhood, lymphocytic lymphoma cancer of the bladder, cancer of the kidney or reter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

In yet another further embodiment the present invention provides a method of treating an infectious disease in a subject comprising administering to the subject a therapeutically effective amount of the compound of the present invention or a pharmaceutical composition thereof capable of inhibiting the programmed cell death 1 (PD1) signalling pathway such that the subject is treated for the infectious disease.

Still yet another embodiment of the present invention provides a method of treating bacterial, viral and fungal infections in a subject comprising administering to the subject a therapeutically effective amount of the compound of the present invention or a pharmaceutical composition thereof capable of inhibiting the programmed cell death 1 (PD1) signaling pathway such that the subject is treated for the bacterial, viral and fungal infections.

The infectious disease includes but not limited to HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, E. Coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus (fumiga-*

*tus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

The compounds of the present invention may be used as single drugs or as a pharmaceutical composition in which the compound is mixed with various pharmacologically acceptable materials.

The pharmaceutical composition is usually administered by oral or inhalation routes, but can be administered by parenteral administration route. In the practice of this invention, compositions can be administered, for example, by orally, intravenous infusion, topically, intraperitoneally, intravesically or intrathecally. Examples of the parenteral administration includes but not limited to intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Oral administration, parenteral administration, subcutaneous administration and intravenous administration are the preferred methods of administration.

The dosage of the compounds of the present invention varies depending on age, weight, symptom, therapeutic efficacy, dosing regimen and/or treatment time. Generally, they may be administered by oral or inhalation routes, in an amount of 1 mg to 100 mg per time, from once a couple of days, once 3 days, once 2 days, once a day to a couple of times a day, in the case of an adult, or continuously administered by oral or inhalation routes from 1 to 24 hours a day. Since the dosage is affected by various conditions, an amount less than the above dosage may sometimes work well enough, or higher dosage may be required in some cases.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the compounds of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutropenia) treatment drug, thrombocytopenia treatment drug, antiemetic and cancer pain intervention drug, concomitantly or in a mixture form.

In one embodiment, the compound(s) of the present invention can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-$\alpha$, $\beta$, or $\gamma$, IL-1, IL-2, IL-3, IL-12, Poly (I:C) and $C_pG$.

In another embodiment, the potentiating agents includes cyclophosphamide and analogs of cyclophosphamide, anti-TGF$\beta$ and Imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term 'compound(s)' refers to the compounds disclosed in the present invention.

As used herein, the term "comprise" or "comprising" is generally used in the sense of include, that is to say permitting the presence of one or more features or components.

As used herein, the term "including" as well as other forms, such as "include", "includes," and "included," is not limiting.

As used herein, the term "optionally substituted" refers to the replacement of one or more hydrogen radicals in a given structure with the radical of a specified substituent including, but not limited to: alkyl, alkoxy, acyl, halo, and hydroxyl. It is understood that the substituent may be further substituted.

As used herein the term "alkyl" refers to a hydrocarbon chain radical that includes solely carbon and hydrogen atoms in the backbone, containing no unsaturation, having from one to twenty carbon atoms (i.e., $C_{1-20}$ alkyl) or one to ten carbon atoms (i.e., $C_{1-10}$ alkyl) or one to five carbon atoms (i.e., $C_{1-5}$ alkyl) and which is attached to the rest of the molecule by a single bond, e.g., including but not limited to methyl, ethyl, propyl, butyl, isobutyl, sec-butyl, tert-butyl, isopentyl or neopentyl. Unless set forth or recited to the contrary, all alkyl groups described or claimed herein may be straight chain or branched, substituted or unsubstituted.

As used herein, the term "acyl" refers to RC(O)—, wherein R is alkyl as defined above. Examples of acyl group include, but are not limited to —C(O)CH$_3$, —C(O)CH$_2$CH$_3$, —C(O)(CH$_2$)$_2$CH$_3$, —C(O)(CH$_2$)$_3$CH$_3$, —C(O)(CH$_2$)$_4$CH$_3$, —C(O)(CH$_2$)$_5$CH$_3$, —C(O)(CH$_2$)$_6$CH$_3$ and —C(O)(CH$_2$)$_8$CH$_3$.

As used herein, the term "amidated C-terminus" refers to that the C-terminal of the amino acid in amide form.

As used herein, the term "amide form" refers to primary, secondary and/or tertiary amides and may be represented by the formula —C(O)NR$_x$R$_y$, wherein each of R$_x$ and R$_y$ independently represents hydrogen or alkyl.

As used herein, the term "amino" refers to —NH$_2$ group. Unless set forth or recited to the contrary, all amino groups described or claimed herein may be substituted or unsubstituted.

As used herein, the term "amino acid" refers to amino acids having L or D stereochemistry at the alpha carbon. Optional substituent on amino acid means replacement of one or more hydrogen radicals in a given structure with the radical of a specified substituent, in case of amino acid containing hydroxyl group such as Serine or Threonine, the hydroxyl group can be substituted with the specified substituent.

As used herein, the term "aryl" refers to $C_4$-$C_{10}$ carbocyclic aromatic system containing one or two rings wherein such rings may be fused. Examples of aryl groups include, but are not limited to phenyl and naphthyl.

As used herein, the term "arylalkyl" refers to an aryl group as defined above directly bonded to an alkyl group (e.g., benzyl and the like).

As used herein, the term "carboxylic acid" refers to —COOH group.

As used herein, the term "coupling agent" means a compound that reacts with the hydroxyl moiety of a carboxy moiety thereby rendering it susceptible to nucleophilic attack. Coupling agents of this type are known in the art and include, but are not limited to, EDCI, HATU, HOBt, DIC and DCC.

As used herein the term "ester" refers to ($C_1$-$C_6$) linear or branched alkyl, ($C_4$-$C_{10}$)aryl, ($C_4$-$C_{10}$)heteroaryl or arylalkyl esters.

As used herein the term "esterified C-terminus" refers to that the C-terminal of the amino acid in ester form.

As used herein the term "free C-terminus' refers to that the C-terminal of the amino acid in —CO$_2$H form.

As used herein, the terms "halogen" or "halo" includes fluorine, chlorine, bromine or iodine.

As used herein the term "Hydroxy" or "Hydroxyl" refers to —OH group.

"Pharmaceutically acceptable salt" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomer/stereoisomers" refers to any enantiomers, diastereoisomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

The term "subject" includes mammals (especially humans) and other animals, such as domestic animals (e.g., household pets including cats and dogs) and non-domestic animals (such as wildlife).

The phrase "therapeutically effective amount" or "efficient amount" refers to sufficient amount of the compound (s) of the present invention that (i) treats or prevents the particular disease, disorder or syndrome (ii) attenuates, ameliorates or eliminates one or more symptoms of the particular disease, disorder or syndrome or (iii) prevents or delays the onset of one or more symptoms of the particular disease, disorder or syndrome described herein. In the case of cancer, the therapeutically effective amount of the drug may decrease the number of cancer cells; decrease the cancer size; inhibit (i.e., slow to some extent and alternatively stop) cancer cell infiltration into peripheral organs; suppress (i.e., slow to some extent and alternatively stop) tumor metastasis; inhibit, to some extent, tumor growth; and/or relieve to some extent one or more of the symptoms associated with the cancer. In the case of infectious disease states, the therapeutic effective amount is an amount sufficient to decrease or alleviate an infectious diseases, the symptoms of an infections caused by bacterial, viral and fungal.

Naturally-occurring amino acids are identified throughout the specification by the conventional three-letter abbreviations indicated in the below Table 2.

TABLE 2

(Amino acid codes)

| Name | 3-letter code |
|---|---|
| Asparagine | Asn |
| Aspartic acid | Asp |
| Glutamic acid | Glu |
| Glutamine | Gln |
| Serine | Ser |
| Threonine | Thr |

The abbreviations used in the entire specification may be summarized herein below with their particular meaning.

° C. (degree Celsius); δ (delta); % (percentage); brine (NaCl solution); CDI CH$_2$Cl$_2$/DCM (Dichloromethane); DMF (Dimethyl formamide); DMSO (Dimethyl sulphoxide); DCC (Dicyclohexylcarbodiimide); DIC (N,N'-diisopropylcarbodiimide); DMSO-d$_6$ (Deuterated DMSO); EDC.HCl/EDCI (1-(3-Dimethyl aminopropyl)-3-carbodiimide hydrochloride); Et$_2$NH (Diethyl amine); EtOH (Ethanol); EtOAc (Ethyl acetate); ECF (ethylchloroformate); Fmoc (Fluorenylmethyloxycarbonyl chloride); g or gr (gram); H or H$_2$ (Hydrogen); H$_2$O (Water); HOBt/HOBT (1-Hydroxy benzotriazole); HCl (Hydrochloric acid); h or hr (Hours); HATU (2-(1H-7-Azabenzotriazol-1-yl)-1,1,3,3-tetramethyl uranium hexafluoro phosphate methanaminium); Hz (Hertz); HPLC (High-performance liquid chromatography); K$_2$CO$_3$ (Potassium carbonate); LiOH (Lithium hydroxide); LCMS (Liquid chromatography mass spectroscopy); mmol (Millimoles); M (Molar); μl (Micro litre); mL (Millilitre); mg (Milligram); m (Multiplet); MHz (Megahertz); MS (ES) (Mass spectroscopy-electro spray); min. (Minutes); Na (Sodium); NaHCO$_3$ (Sodium bicarbonate); NaOAc (Sodium acetate); NMM (N-methyl morpholine); Na$_2$SO$_4$ (Sodium sulphate); N$_2$ (Nitrogen); NMR (Nuclear magnetic resonance spectroscopy); NH$_3$ (Ammonia); NH$_2$OH.HCl (Hydroxylamine hydrochloride; PD-L1 (Programmed death-ligand 1); PD-L2 (Programmed cell death 1 ligand 2); prep-HPLC/preparative HPLC (Preparative High-performance liquid chromatography); S (Singlet); $^t$Bu (tertiary butyl); TEA/Et$_3$N (Triethyl amine); TFA (Trifluoroaceticacid); TFAA (Trifluroacetic anhydride); TLC (Thin Layer Chromatography); THF (Tetrahydrofuran); TIPS (Triisopropylsilane); TFA/CF$_3$COOH (Trifluoroacetic acid); t (Triplet); t$_R$=(Retention time); Trt (Triphenyl methane); etc.

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The starting materials are generally available from commercial sources such as Sigma-Aldrich, USA or Germany; Chem-Impex USA; G.L. Biochem, China and Spectrochem, India.

Purification and Characterization of Compounds

Analytical HPLC method: Analytical HPLC was performed using on ZIC HILIC 200 A° column (4.6 mm×250 mm, 5 μm), Flow rate: 1.0 mL/min. The elution conditions used are: Buffer A: 5 mmol ammonium acetate, Buffer B: Acetonitrile, Equilibration of the column with 90% buffer B and elution by a gradient of 90% to 40% buffer B during 30 min.

Preparative HPLC Method: Preparative HPLC was performed using on SeQuant ZIC HILIC 200 A° column (10 mm×250 mm, 5 μm), Flow rate: 5.0 mL/min. The elution conditions used are: Buffer A: 5 mmol ammonium acetate (adjust to pH-4 with Acetic Acid), Buffer B: Acetonitrile, Equilibration of the column with 90% buffer B and elution by a gradient of 90% to 40% buffer B during 20 min.

LCMS was performed on AP1 2000 LC/MS/MS triple quad (Applied bio systems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

EXAMPLE 1

Synthesis of Compound 1

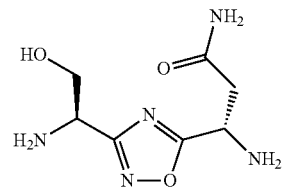

FIG. 1A illustrates Steps 1a, 1b and 1c.

Step 1a: Ethylchloroformate (1.5 g, 13.78 mmol) and N-Methylmorpholine (1.4 g, 13.78 mmol) were added to a solution of compound 1a (3 g, 11.48 mmol) in THF (30 mL) and stirred at −20° C. After 20 min. liquid ammonia (0.77 g, 45.92 mmol) was added to the active mixed anhydride formed in-situ and stirred at 0-5° C. for 20 min. The completeness of the reaction was confirmed by TLC analysis. The reaction mixture was evaporated under reduced pressure and partitioned between water and ethyl acetate. Organic layer was washed with NaHCO$_3$, citric acid, brine solution, dried over Na$_2$SO$_4$ and evaporated under reduced pressure to get 2.9 g of compound 1b (Yield: 96.3%). LCMS: 261.0 (M+H)$^+$.

Step 1b: Trifluroacetic anhydride (9.7 g, 46.0 mmol) was added to a solution of compound 1b (8 g, 30.7 mmol) in pyridine (24.3 g, 307.0 mmol) and stirred at room temperature for 3 h. The completeness of the reaction was confirmed by TLC analysis. The reaction mixture was evaporated under reduced pressure and partitioned between water and ethyl acetate. Organic layer was washed with NaHCO$_3$, citric acid, brine solution, dried over Na$_2$SO$_4$ and evaporated under reduced pressure to afford 7 g of compound 1c (Yield: 94.0%). LCMS: 187.2 (M−$^t$Bu)$^+$.

Step 1c: Hydroxylamine hydrochloride (3 g, 43.37 mmol) and potassium carbonate (6 g, 43.37 mmol) were added to a solution of compound 1c (7 g, 28.01 mmol) in EtOH (70 mL) and stirred at 90° C. for 2 h. The completeness of the reaction was confirmed by TLC analysis. The reaction mixture was evaporated under reduced pressure and partitioned between water and ethyl acetate. Organic layer was washed with brine solution, dried over Na$_2$SO$_4$ and evaporated under reduced pressure. The crude compound was purified by silica gel column chromatography (Eluent: 0-5% ethyl acetate in hexane) to get 4.2 g of compound 1d (Yield: 52.8%). LCMS: 276.4 (M+H)$^+$.

Step 1d: Deoxo-Fluor® (1.83 g, 8.3 mmol) was added to a solution of Fmoc-Asn(Trt)-OH (4.5 g, 7.5 mmol) in CH$_2$Cl$_2$ (50 mL) and stirred at 0° C. for 3 h. Then CH$_2$Cl$_2$ was evaporated and triturated with hexane, decanted and evaporated under vacuum to get the corresponding acid fluoride. NMM (1.17 g, 11.6 mmol) and compound 1 d (1.6 g, 5.8 mmol) in THF were added to the acid fluoride and stirred at room temperature for 12 h. Then THF was evaporated and sodium acetate (0.72 g, 8.7 mmol) was added followed by EtOH (50 mL). The reaction mixture was stirred at 90° C. for 2 h. The completeness of the reaction was confirmed by TLC analysis. The reaction mixture was evaporated under reduced pressure and partitioned between water and ethyl acetate. Organic layer was washed with NaHCO$_3$, citric acid, brine solution, dried over Na$_2$SO$_4$ and evaporated under reduced pressure, which was further purified by silica gel column chromatography (Eluent: 0-5% ethyl acetate in hexane) to afford 2.8 g of compound 1e (Yield: 44.4%). LCMS: 836.4 (M+H)$^+$.

Step 1e: To compound 1e (2.3 g, 2.7 mmol) in CH$_2$Cl$_2$ (10 mL) diethylamine (10 mL) was added and the reaction mixture was stirred at room temperature for 30 min. The resulting solution was concentrated in vacuum to get gummy residue. The crude compound was purified by neutral alumina column chromatography (Eluent: 0-50% ethyl acetate in hexane then 0-5% methanol in chloroform) to get 1.4 g of 1f (Yield: 90%). LCMS: 636.5 (M+Na)$^+$.

Step 1f: To a solution of compound 1f (0.45 g) in CH$_2$Cl$_2$ (5 mL), trifluoroacetic acid (5 mL) and catalytic amount of triisopropylsilane were added and stirred for 3 h at room temperature to remove the acid sensitive protecting groups. The resulting solution was concentrated in vacuum to afford 0.29 g of crude compound 1 which was purified using prep-HPLC method described under experimental conditions. $^1$H NMR (DMSO-d$_6$, 400 MHz): δ 2.58 (m, 2H), 3.53 (m, 3H), 3.91 (t, 1H), 4.36 (t, 1H), 6.91 (s, 1H), 7.45 (s, 1H); $^{13}$C NMR (DMSO-d$_6$, 400 MHz): δ 20.85, 45.71, 50.23, 65.55, 171.03, 171.41, 181.66. LCMS: 216.2 (M+H)$^+$; HPLC: t$_R$=13.1 min.

EXAMPLE 2

Synthesis of Compound 2

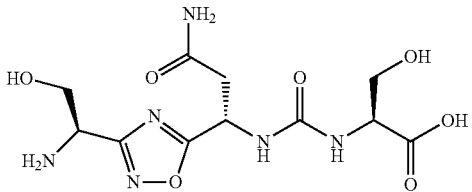 [SMILES: NC(=O)C[C@H](NC(=O)N[C@@H](CO)C(=O)O)c1nc([C@@H](N)CO)no1]

Figure 2:
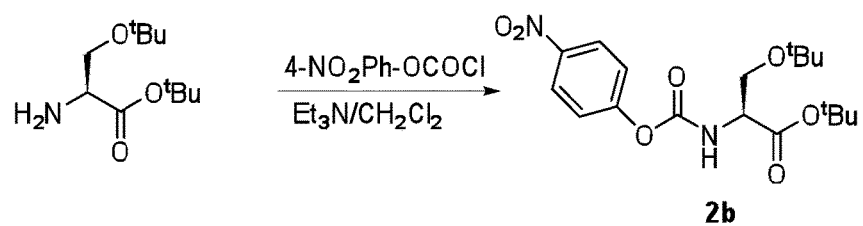
FIG. 2 depicts the chemical synthetic scheme for Compound 2.
Figure 2:
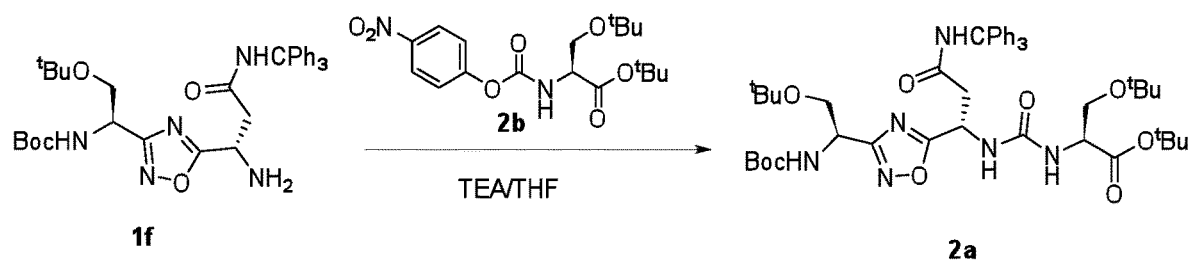
Figure 2:
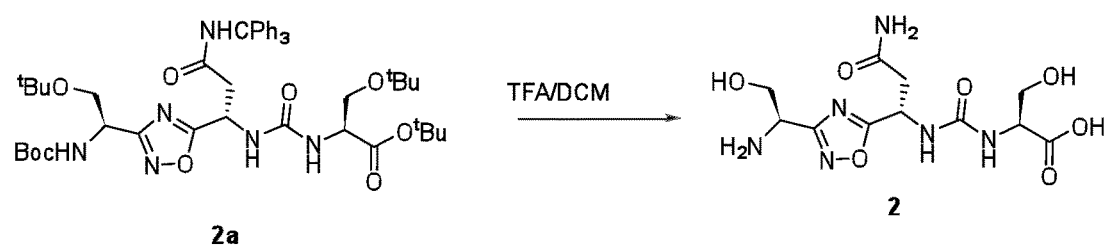

FIG. 2 illustrates Steps 2a and 2b.

Step 2a: The urea linkage was carried out by the coupling compound 1f (2.7 g, 4.39 mmol) in THF (30 mL) at room temperature with compound 2b (1.67 g, 4.39 mmol). The coupling was initiated by the addition of TEA (0.9 g, 8.78 mmol) in THF (10 mL) and the resultant mixture was stirred at room temperature. After completion of 20 h, THF was evaporated from the reaction mass, and partitioned between water and ethyl acetate. Organic layer was washed with water, brine, dried over Na$_2$SO$_4$ and evaporated under reduced pressure to get compound 2a, which was further purified by silica gel column chromatography (Eluent: 0-50% ethyl acetate in hexane) to afford 3.46 g of compound 2a (Yield: 92.10%). LCMS 857.4 (M+H)$^+$.

Step 2b: To a solution of compound 2a (0.22 g, 0.25 mmol) in CH$_2$Cl$_2$ (5 mL), trifluoroacetic acid (5 mL) and catalytic amount of triisopropylsilane were added and stirred for 3 h at room temperature. The resulting solution was concentrated under reduced pressure to obtain 0.35 g of crude compound. The crude solid material was purified using preparative-HPLC method described under experimental conditions. LCMS: 347.1 (M+H)$^+$; HPLC: t$_R$=12.9 min.

Synthesis of Compound 2b (NO$_2$—C$_6$H$_4$—OCO-Thr (O$^t$Bu)—O$^t$Bu)

To the compound H-Ser($^t$Bu)—O$^t$Bu (2 g, 9.2 mmol) in CH$_2$Cl$_2$ (20 mL), triethylamine (1.39 g, 13.8 mmol) was added and the solution was stirred at room temperature for 5-10 min. To this mixture, solution of 4-Nitrophenyl chloroformate (2.22 g, 11.04 mmol) in CH$_2$Cl$_2$ was added and the resultant mixture was stirred at room temperature for 30 min. The completion of the reaction was confirmed by TLC analysis. After completion of reaction, reaction mixture was diluted with CH$_2$Cl$_2$ and washed with water and 5.0 M citric acid solution, dried over Na$_2$SO$_4$ and evaporated under reduced pressure to get crude compound 2b, which was further purified by silica gel column chromatography (Eluent: 0-20% ethyl acetate in hexane) to yield 2.1 g (58.9%) of 2b.

EXAMPLE 3

Synthesis of Compound 3

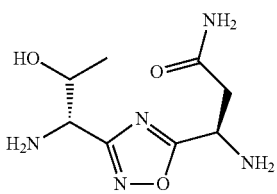 [SMILES: CC(O)[C@@H](N)c1noc([C@H](N)CC(N)=O)n1]

The compound was synthesised using similar procedure as depicted in Example 1 (compound 1) and D-amino acids are linked up in reverse order. Boc-D-Thr($^t$Bu)—OH was used in place of Boc-Ser($^t$Bu)—OH (compound 1a, Example 1) and Fmoc-D-Asn(trt)-OH in place of Fmoc-Asn (trt)-OH to yield 0.15 g crude material of the title compound 3. LCMS: 230.1 (M+H)$^+$.

EXAMPLE 4

Synthesis of Compound 4

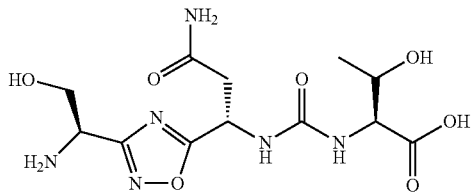 [SMILES: CC(O)[C@H](NC(=O)N[C@@H](CC(N)=O)c1nc([C@@H](N)CO)no1)C(=O)O]

The compound was synthesised using similar procedure as depicted in Example 2 for synthesising compound 2 using H-Thr($^t$Bu)—O$^t$Bu instead of H-Ser($^t$Bu)—O$^t$Bu (in synthesis of compound 2b) to yield 0.35 g crude material of the title compound. The crude solid material was purified using preparative HPLC described under experimental conditions. LCMS: 361.2 (M+H)$^+$, HPLC: $t_R$=12.19 min.

EXAMPLE 5

Synthesis of Compound 5

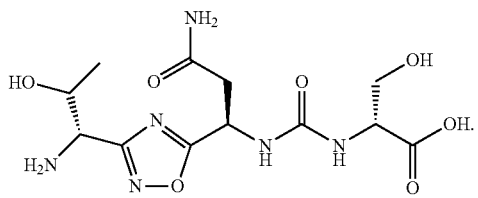 [SMILES: CC(O)[C@@H](N)c1noc([C@@H](CC(N)=O)NC(=O)N[C@H](CO)C(=O)O)n1]

The compound was synthesised using similar procedure as depicted in Example 4 (compound 4) using D-amino acids are linked up in reverse order. Boc-D-Thr($^t$Bu)—OH was used in place of Boc-Ser($^t$Bu)—OH, Fmoc-D-Asn(trt)-OH in place of Fmoc-Asn(trt)-OH and H-D-Ser($^t$Bu)—O$^t$Bu was used in place of H-Thr($^t$Bu)—O$^t$Bu to yield 0.3 g crude material of the title compound. The crude solid material was purified using preparative HPLC described under experimental conditions. LCMS: 361.3 (M+H)$^+$. HPLC: $t_R$=13.58 min.

EXAMPLE 6

Synthesis of Compound 6

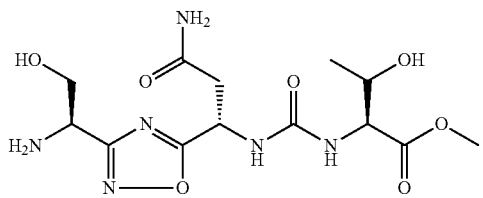 [SMILES: COC(=O)[C@@H](NC(=O)N[C@@H](CC(N)=O)c1nc([C@@H](N)CO)no1)C(C)O]

The compound was synthesised using similar procedure as depicted in Example 2 by using H-Thr($^t$Bu)—OMe instead of H-Ser($^t$Bu)—O$^t$Bu (in synthesis of compound 2b) to yield 0.2 g crude material of the title compound. The crude solid material was purified using preparative HPLC described under experimental conditions. LCMS: 375.1 (M+H)$^+$, HPLC: $t_R$=11.84 min.

EXAMPLE 7

Synthesis of Compound 7

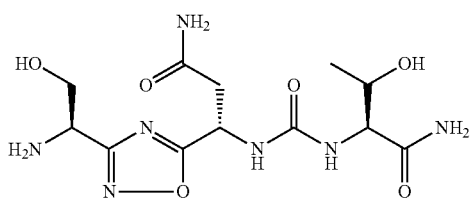 [SMILES: CC(O)[C@H](NC(=O)N[C@@H](CC(N)=O)c1nc([C@@H](N)CO)no1)C(N)=O]

Figure 3:
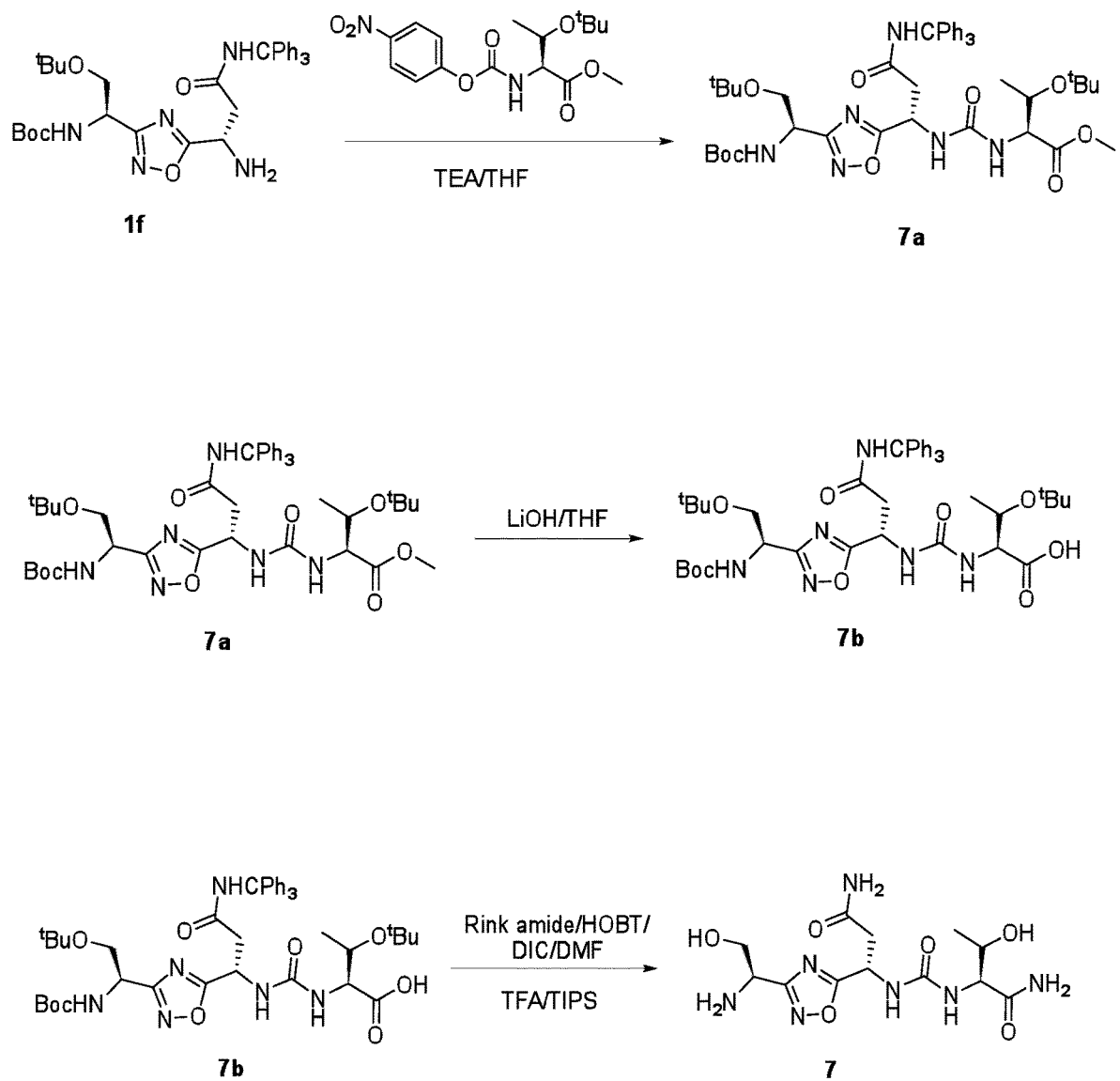
FIG. 3 depicts the chemical synthetic scheme for Compound 7.

FIG. 3 illustrates Steps 7a, 7b and 7c.

Step 7a: The compound 7a was synthesised using similar procedure as for compound 2a (Example 2, step 2a) using H-Thr($^t$Bu)—OMe instead of H-Ser($^t$Bu)—OtBu to get crude material which was further purified by silica gel column chromatography (Eluent: 0-50% ethyl acetate in hexane) to get 2.0 g of compound 7a (Yield: 74%). LCMS: 829.2 (M+H)$^+$.

Step 7b: To a solution of compound 7a (0.35 g, 4.0 mmol) in THF (5 mL) was added lithium hydroxide (0.026 g, 0.63 mmol) at 0° C. and the mixture was stirred for 2 h at room temperature. The completion of the reaction was confirmed by TLC analysis. THF was evaporated from the reaction mass, and partitioned between water and ethyl acetate. Organic layer was washed with citric acid, brine solution, dried over Na$_2$SO$_4$ and evaporated under reduced pressure to afford 7b, which was further purified by silica gel column chromatography (Eluent: 0-5% methanol in DCM) to get 0.3 g of product 7b (Yield: 86.7%). LCMS 815.2 (M+H)$^+$.

Step 7c: Compound 7b (0.295 g, 0.39 mmol) was anchored to Rink amide resin (0.7 g, 0.55 mmol/g) using HOBT (0.072 g, 0.54 mmol) and DIC (0.068 g, 0.54 mmol) method in DMF (10 mL). The resin was stirred for 12 h at room temperature. The resin was washed with DCM, DMF and DCM and dried. The target compound was cleaved from the rink amide resin using TFA (5 mL) and catalytic amount of TIPS. The resin was allowed to remain at room temperature for 2 h with occasional stirring. After 2 h, TFA and TIPS were evaporated under nitrogen atmosphere and the resulting residue was washed with diethyl ether to yield 0.1 g crude material of the title compound 7. The crude solid material was purified using preparative HPLC described under experimental conditions. LCMS: 360.0 (M+H)$^+$, HPLC: $t_R$=13.88 min.

EXAMPLE 8

Synthesis of Compound 8

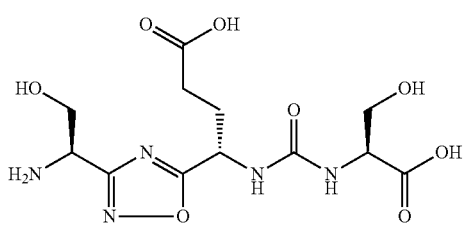

The compound was synthesised using similar procedure as depicted in Example 2 (compound 2) using Fmoc-Glu (O'Bu)—OH instead of Fmoc-Asn(Trt)-OH to get 0.4 g crude material of the title compound. The crude solid material was purified using preparative HPLC described under experimental conditions. LCMS: 362.1 (M+H)$^+$. HPLC: $t_R$=13.27 min.

The compounds in Table 3 below were prepared based on the experimental procedures described above.

TABLE 3

| Compound No. | Structure | LCMS (M + H)$^+$ | HPLC ($t_R$ in min.) |
|---|---|---|---|
| 9 | 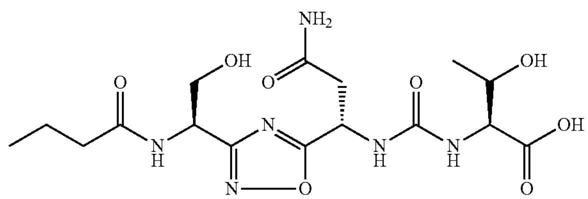 [SMILES: CCCC(=O)N[C@@H](CO)c1noc([C@H](CC(N)=O)NC(=O)N[C@H](C(=O)O)C(C)O)n1] | 431.1 | 4.64 |
| 10 | 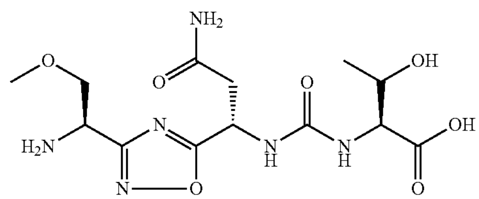 [SMILES: COC[C@H](N)c1noc([C@H](CC(N)=O)NC(=O)N[C@H](C(=O)O)C(C)O)n1] | 375.2 | 11.13 |
| 11 | 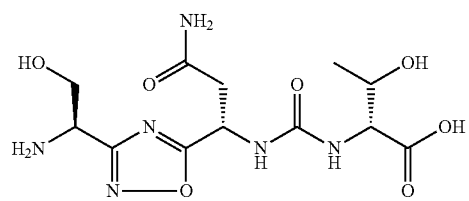 [SMILES: CC(O)[C@@H](NC(=O)N[C@@H](CC(N)=O)c1nc([C@@H](N)CO)no1)C(=O)O] | 361.2 | 11.85 |
| 12 | 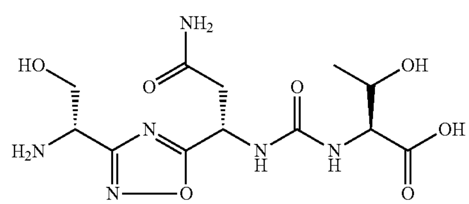 [SMILES: CC(O)[C@H](NC(=O)N[C@@H](CC(N)=O)c1nc([C@H](N)CO)no1)C(=O)O] | 361.2 | 12.38 |
| 13 | 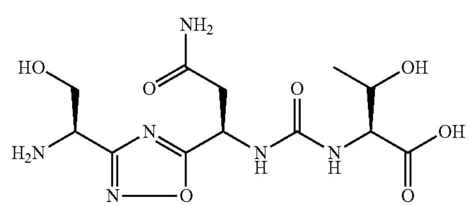 [SMILES: CC(O)[C@H](NC(=O)N[C@H](CC(N)=O)c1nc([C@@H](N)CO)no1)C(=O)O] | 361.2 | 12.02 |
| 14 | 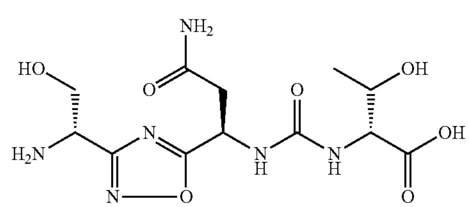 [SMILES: CC(O)[C@@H](NC(=O)N[C@H](CC(N)=O)c1nc([C@H](N)CO)no1)C(=O)O] | 375.1 | 11.74 |

TABLE 3-continued

| Compound No. | Structure | LCMS (M + H)+ | HPLC (t_R in min.) |
|---|---|---|---|
| 15 | 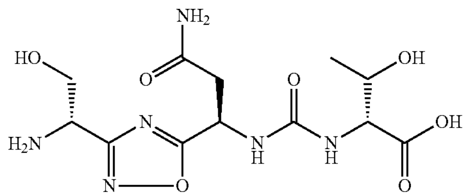 [SMILES: CC(O)[C@@H](NC(=O)N[C@H](CC(N)=O)c1nc([C@H](N)CO)no1)C(=O)O] | 361.1 | 12.41 |
| 16 | 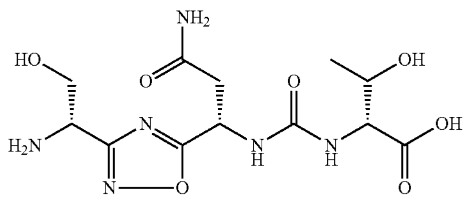 [SMILES: CC(O)[C@@H](NC(=O)N[C@@H](CC(N)=O)c1nc([C@H](N)CO)no1)C(=O)O] | 361.1 | 12.34 |
| 17 | 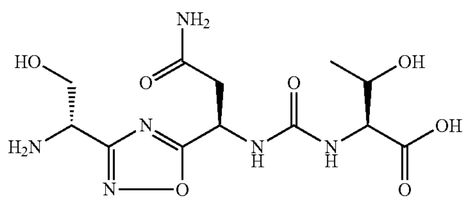 [SMILES: CC(O)[C@H](NC(=O)N[C@H](CC(N)=O)c1nc([C@H](N)CO)no1)C(=O)O] | 361.2 | 12.62 |
| 18 | 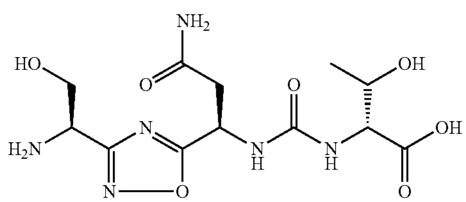 [SMILES: CC(O)[C@@H](NC(=O)N[C@H](CC(N)=O)c1nc([C@@H](N)CO)no1)C(=O)O] | 361.2 | 12.87 |
| 19 | 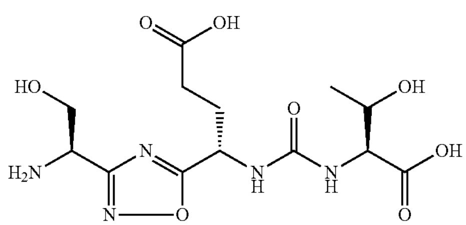 [SMILES: CC(O)[C@H](NC(=O)N[C@@H](CCC(=O)O)c1nc([C@@H](N)CO)no1)C(=O)O] | 376.1 | 12.41 |
| 20 | 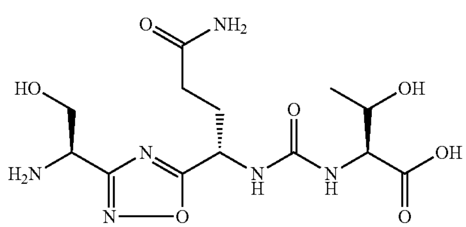 [SMILES: CC(O)[C@H](NC(=O)N[C@@H](CCC(N)=O)c1nc([C@@H](N)CO)no1)C(=O)O] | 375.1 | 12.31 |
| 21 | 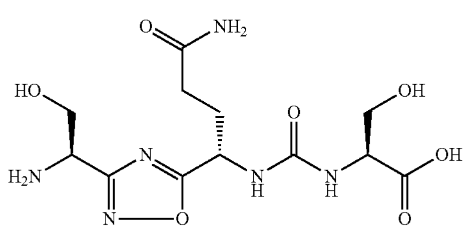 [SMILES: NC(=O)CC[C@H](NC(=O)N[C@@H](CO)C(=O)O)c1nc([C@@H](N)CO)no1] | 361.3 | 13.19 |

TABLE 3-continued

| Compound No. | Structure | LCMS (M + H)+ | HPLC ($t_R$ in min.) |
|---|---|---|---|
| 22 | 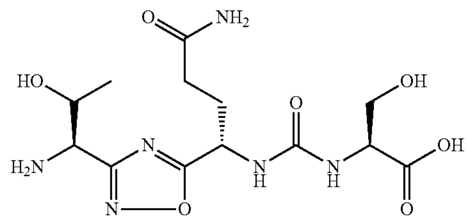 [SMILES: CC(O)[C@H](N)c1noc([C@H](CCC(N)=O)NC(=O)N[C@@H](CO)C(=O)O)n1] | 375.1 | 12.52 |
| 23 | 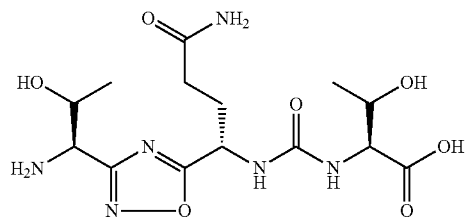 [SMILES: CC(O)[C@H](NC(=O)N[C@@H](CCC(N)=O)c1nc([C@@H](N)C(C)O)no1)C(=O)O] | 389.2 | 12.07 |
| 24 | 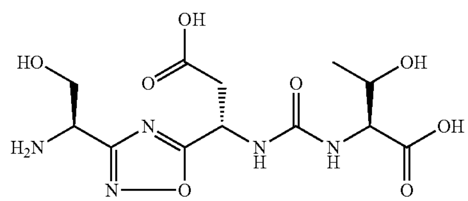 [SMILES: CC(O)[C@H](NC(=O)N[C@@H](CC(=O)O)c1nc([C@@H](N)CO)no1)C(=O)O] | 362.2 | 12.78 |
| 25 | 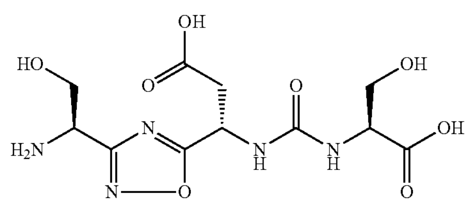 [SMILES: N[C@@H](CO)c1noc([C@H](CC(=O)O)NC(=O)N[C@@H](CO)C(=O)O)n1] | 348.2 | 13.21 |

EXAMPLE 9

Rescue of Mouse Splenocyte Proliferation in Presence of Recombinant PD-L1/PD-L2

Recombinant mouse PD-L1 (rm-PDL-1, cat no: 1019-B7-100 & rh-PDL-1, cat no: 156-B7-100, R&D Systems) were used as the source of PD-L1.

Requirement

Mouse splenocytes harvested from 6-8 weeks old C57 BL6 mice; RPMI 1640 (GIBCO, Cat #11875); DMEM with high glucose (GIBCO, Cat #D6429); Fetal Bovine Serum [Hyclone, Cat #SH30071.03]; Penicillin (10000 unit/mL)-Streptomycin(10,000 µg/mL) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density-1.083 gm/mL) (SIGMA 10831); Trypan blue solution (SIGMA-T8154); 2 mL Norm Ject Luer Lock syringe-(Sigma 2014-12); 40 µm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Dimethyl sulfoxide (DMSO $C_2H_6SO$, SIGMA-D-5879) and aliquoted in to tubes for further use. Working concentrations were titrated from 10 µM to 1 µM. (eBioscience—650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).

Protocol

Splenocyte Preparation and Culturing

Splenocytes harvested in a 50 mL falcon tube by mashing mouse spleen in a 40 µm cell strainer were further treated with 1 mL ACK lysis buffer for 5 min at room temperature. After washing with 9 mL of RPMI complete media, cells were re-suspended in 3 mL of 1×PBS in a 15 mL tube. 3 mL of Histopaque was added carefully to the bottom of the tube without disturbing overlaying splenocyte suspension. After centrifuging at 800×g for 20 min at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+10,000 units/mL penicillin and 10,000 μg/mL streptomycin) and maintained in a $CO_2$ incubator with 5% $CO_2$ at 37° C.

CFSE Proliferation Assay

CFSE is a dye that passively diffuses into cells and binds to intracellular proteins. $1 \times 10^6$ cells/mL of harvested splenocytes were treated with 5 μM of CFSE in pre-warmed 1×PBS/0.1% BSA solution for 10 min at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1 \times 10^5$ splenocytes added to wells containing either MDA-MB231 cells ($1 \times 10^5$ cells cultured in high glucose DMEM medium) or recombinant human PDL-1 (100 ng/mL) and test compounds. Splenocytes were stimulated with anti-mouse CD3 and anti-mouse CD28 antibody (1 μg/mL each), and the culture was further incubated for 72 h at 37° C. with 5% $CO_2$. Cells were harvested and washed thrice with ice cold FACS buffer and % proliferation was analyzed by flow cytometry with 488 nm excitation and 521 nm emission filters.

Data Compilation, Processing and Inference

Percent splenocyte proliferation was analyzed using cell quest FACS program and percent rescue of splenocyte proliferation by compound was estimated after deduction of % background proliferation value and normalising to % stimulated splenocyte proliferation (positive control) as 100%.
Stimulated splenocytes: Splenocytes+anti-CD3/CD28 stimulation
Background proliferation: Splenocytes+anti-CD3/CD28+PD-L1
Compound proliferation: Splenocytes+anti-CD3/CD28+PD-L1+Compound
Compound effect is examined by adding required conc. of compound to anti-CD3/CD28 stimulated splenocytes in presence of ligand (PDL-1) (Table 4).

TABLE 4

| Compound No. | Percent rescue of splenocyte proliferation @ 100 nM compound concentration |
| --- | --- |
| 1 | 93 |
| 2 | 50 |
| 4 | 89 |
| 5 | 67.6 |
| 6 | 84 |
| 7 | 55 |
| 8 | 67 |
| 9 | 34 |
| 10 | 49 |
| 11 | 90 |
| 12 | 64 |
| 13 | 74 |
| 14 | 75 |
| 15 | 83 |
| 16 | 72 |
| 17 | 55 |
| 18 | 64 |
| 19 | 88 |
| 20 | 69 |
| 21 | 47 |

TABLE 4-continued

| Compound No. | Percent rescue of splenocyte proliferation @ 100 nM compound concentration |
| --- | --- |
| 22 | 55 |
| 23 | 74 |
| 24 | 52 |
| 25 | 91 |

What is claimed is:

1. A method of treating cancer in a subject in need thereof, comprising administering to the subject a compound of formula (I) or a pharmaceutically acceptable salt or a pharmaceutically acceptable composition thereof:

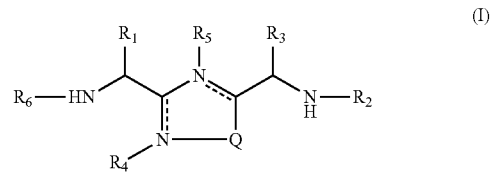

(I)

wherein,
Q is S or O;
$R_1$ represents a side chain of an amino acid residue Ser or Thr, optionally substituted with alkyl or acyl;
$R_2$ is hydrogen or —CO-Aaa;
Aaa is an amino acid residue Thr or Ser; wherein a C-terminus thereof is a free terminus, is amidated, or is esterified;
$R_3$ represents a side chain of an amino acid residue Asn, Asp, Gln, or Glu;
----- is an optional bond;
$R_4$ and $R_5$ independently are hydrogen or absent; and
$R_6$ is hydrogen, alkyl, or acyl.

2. The method according to claim 1, wherein Q is O.
3. The method according to claim 1, wherein $R_6$ is H.
4. The method according to claim 1, wherein $R_6$ is —C(O)CH$_3$, —C(O)CH$_2$CH$_3$, —C(O)(CH$_2$)$_2$CH$_3$, —C(O)(CH$_2$)$_3$CH$_3$, —C(O)(CH$_2$)$_4$CH$_3$, or —C(O)(CH$_2$)$_5$CH$_3$.
5. The method according to claim 1, wherein $R_2$ is —CO-Aaa.
6. The method according to claim 1, wherein the compound of formula (I) is a compound of formula (IA):

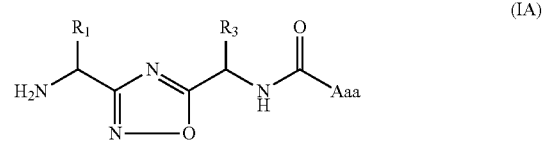

(IA)

or a pharmaceutically acceptable salt thereof; wherein,
$R_1$ represents a side chain of an amino acid residue Ser or Thr, optionally substituted with alkyl or acyl;
$R_3$ represents a side chain of an amino acid residue Asn, Asp, Gln, or Glu; and
Aaa is an amino acid residue Thr or Ser; wherein the C-terminus thereof is a free terminus, is amidated, or is esterified.

7. The method according to claim 1, wherein Aaa is the amino acid residue Thr or Ser; wherein the C-terminus is the free terminus.

8. The method according to claim 1, wherein the compound of formula (I) is a compound of formula (IB):

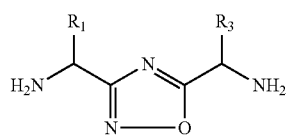

(IB)

or a pharmaceutically acceptable salt thereof; wherein,

R₁ represents a side chain of an amino acid residue Ser or Thr, optionally substituted with alkyl or acyl; and R₃ represents a side chain of an amino acid residue Asn, Asp, Gln, or Glu.

9. The method according to claim 1, wherein R₁ represents the side chain of an amino acid residue Ser or Thr.

10. The method according to claim 1, wherein R₁ is substituted with C₁₋₅ alkyl.

11. The method according to claim 1, wherein R₃ represents the side chain of the amino acid residue Asn or Glu.

12. The method according to claim 1, wherein:

R₁ represents the side chain of an amino acid residue Ser or Thr;

R₂ is —CO-Aaa;

Aaa is the amino acid residue Thr or Ser; wherein the C-terminus is a free terminus; and R₃ represents the side chain of the amino acid residue Asn or Glu.

13. The method according to claim 1, wherein R₁ represents the side chain of the amino acid residue Ser.

14. The method according to claim 1, wherein R₁ represents the side chain of the amino acid residue Thr.

15. The method according to claim 1, wherein Aaa is Ser.

16. The method according to claim 1, wherein Aaa is Thr.

17. The method according to claim 1, wherein R₃ represents the side chain of the amino acid residue Asn.

18. The method according to claim 1, wherein R₃ represents the side chain of the amino acid residue Asp.

19. The method according to claim 1, wherein R₃ represents the side chain of the amino acid residue Gln.

20. The method according to claim 1, wherein R₃ represents the side chain of the amino acid residue Glu.

21. The method according to claim 1, wherein R₂ is H.

22. The method according to claim 1, wherein the compound has the following structure:

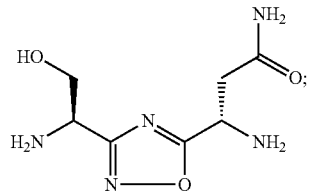 [SMILES: NC(=O)C[C@H](N)c1nc([C@@H](N)CO)no1]

or a pharmaceutically acceptable salt thereof.

23. The method according to claim 1, wherein the compound has the following structure:

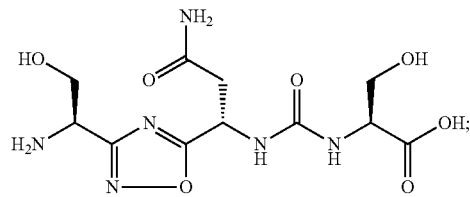 [SMILES: NC(=O)C[C@H](NC(=O)N[C@@H](CO)C(=O)O)c1nc([C@@H](N)CO)no1]

or a pharmaceutically acceptable salt thereof.

24. The method according to claim 1, wherein the compound has the following structure:

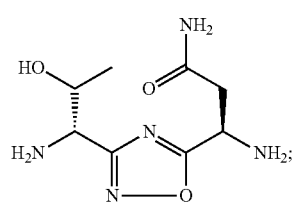 [SMILES: CC(O)[C@@H](N)c1noc([C@H](N)CC(N)=O)n1]

or a pharmaceutically acceptable salt thereof.

25. The method according to claim 1, wherein the compound has the following structure:

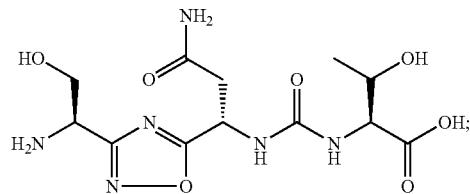

or a pharmaceutically acceptable salt thereof.

26. The method according to claim 1, wherein the compound has the following structure:

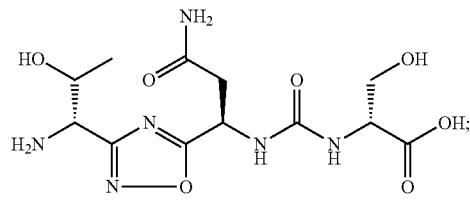 [SMILES: CC(O)[C@@H](N)c1noc([C@@H](CC(N)=O)NC(=O)N[C@H](CO)C(=O)O)n1]

or a pharmaceutically acceptable salt thereof.

27. The method according to claim 1, wherein the compound has the following structure:

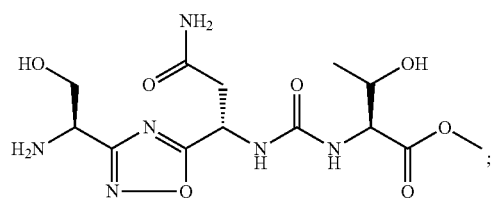 [SMILES: COC(=O)[C@@H](NC(=O)N[C@@H](CC(N)=O)c1nc([C@@H](N)CO)no1)C(C)O]

or a pharmaceutically acceptable salt thereof.

28. The method according to claim 1, wherein the compound has the following structure:

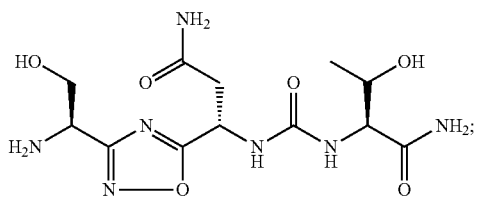 [SMILES: CC(O)[C@H](NC(=O)N[C@@H](CC(N)=O)c1nc([C@@H](N)CO)no1)C(N)=O]

or a pharmaceutically acceptable salt thereof.
29. The method according to claim 1, wherein the compound has the following structure:

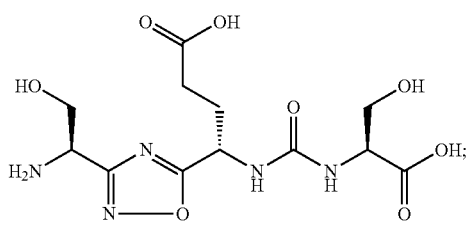 [SMILES: N[C@@H](CO)c1noc([C@H](CCC(=O)O)NC(=O)N[C@@H](CO)C(=O)O)n1]

or a pharmaceutically acceptable salt thereof.
30. The method according to claim 1, wherein the compound has the following structure:

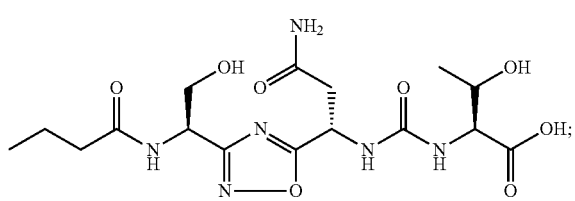 [SMILES: CCCC(=O)N[C@@H](CO)c1noc([C@H](CC(N)=O)NC(=O)N[C@H](C(=O)O)C(C)O)n1]

or a pharmaceutically acceptable salt thereof.
31. The method according to claim 1, wherein the compound has the following structure:

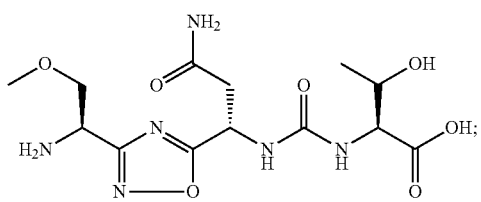 [SMILES: COC[C@H](N)c1noc([C@H](CC(N)=O)NC(=O)N[C@H](C(=O)O)C(C)O)n1]

or a pharmaceutically acceptable salt thereof.
32. The method according to claim 1, wherein the compound has the following structure:

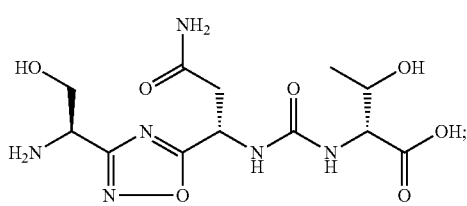 [SMILES: CC(O)[C@@H](NC(=O)N[C@@H](CC(N)=O)c1nc([C@@H](N)CO)no1)C(=O)O]

or a pharmaceutically acceptable salt thereof.
33. The method according to claim 1, wherein the compound has the following structure:

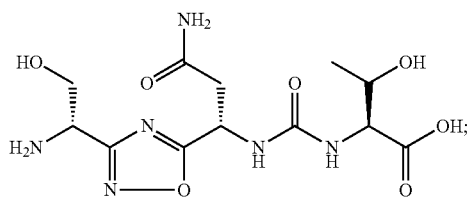 [SMILES: CC(O)[C@H](NC(=O)N[C@@H](CC(N)=O)c1nc([C@H](N)CO)no1)C(=O)O]

or a pharmaceutically acceptable salt thereof.
34. The method according to claim 1, wherein the compound has the following structure:

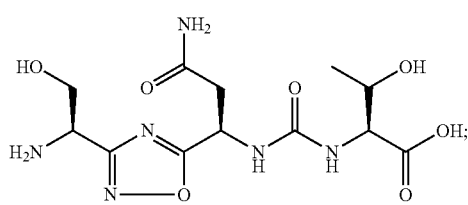 [SMILES: CC(O)[C@H](NC(=O)N[C@H](CC(N)=O)c1nc([C@@H](N)CO)no1)C(=O)O]

or a pharmaceutically acceptable salt thereof.
35. The method according to claim 1, wherein the compound has the following structure:

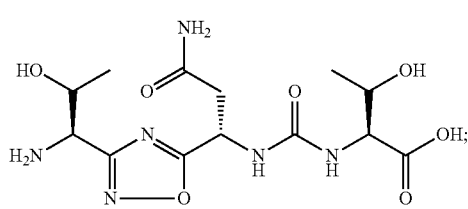 [SMILES: CC(O)[C@H](NC(=O)N[C@@H](CC(N)=O)c1nc([C@@H](N)C(C)O)no1)C(=O)O]

or a pharmaceutically acceptable salt thereof.
36. The method according to claim 1, wherein the compound has the following structure:

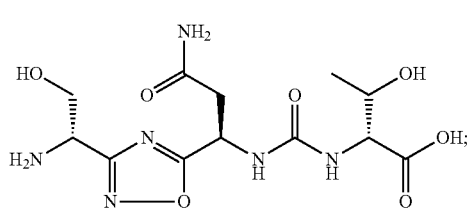 [SMILES: CC(O)[C@@H](NC(=O)N[C@H](CC(N)=O)c1nc([C@H](N)CO)no1)C(=O)O]

or a pharmaceutically acceptable salt thereof.
37. The method according to claim 1, wherein the compound has the following structure:

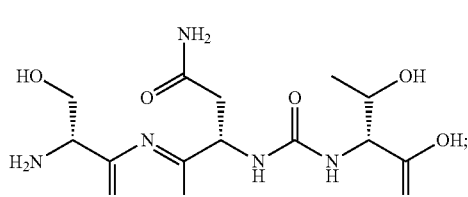

or a pharmaceutically acceptable salt thereof.
38. The method according to claim 1, wherein the compound has the following structure:

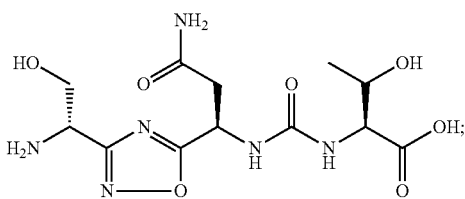 [SMILES: CC(O)[C@H](NC(=O)N[C@H](CC(N)=O)c1nc([C@H](N)CO)no1)C(=O)O]

or a pharmaceutically acceptable salt thereof.

39. The method according to claim 1, wherein the compound has the following structure:

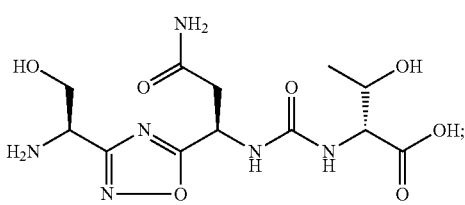 [SMILES: CC(O)[C@@H](NC(=O)N[C@H](CC(N)=O)c1nc([C@@H](N)CO)no1)C(=O)O]

or a pharmaceutically acceptable salt thereof.

40. The method according to claim 1, wherein the compound has the following structure:

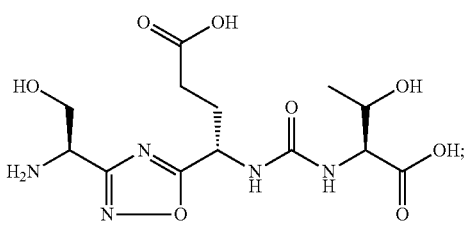

or a pharmaceutically acceptable salt thereof.

41. The method according to claim 1, wherein the compound has the following structure:

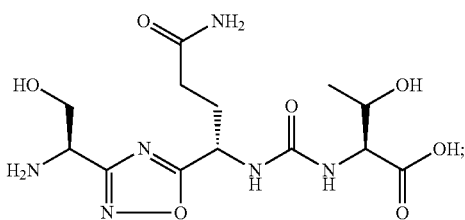 [SMILES: CC(O)[C@H](NC(=O)N[C@@H](CCC(=O)O)c1nc([C@@H](N)CO)no1)C(=O)O]

or a pharmaceutically acceptable salt thereof.

42. The method according to claim 1, wherein the compound has the following structure:

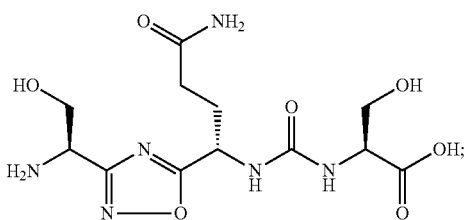

or a pharmaceutically acceptable salt thereof.

43. The method according to claim 1, wherein the compound has the following structure:

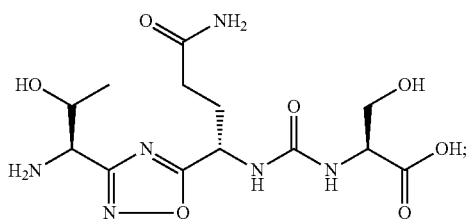 [SMILES: CC(O)[C@H](N)c1noc([C@H](CCC(N)=O)NC(=O)N[C@@H](CO)C(=O)O)n1]

or a pharmaceutically acceptable salt thereof.

44. The method according to claim 1, wherein the compound has the following structure:

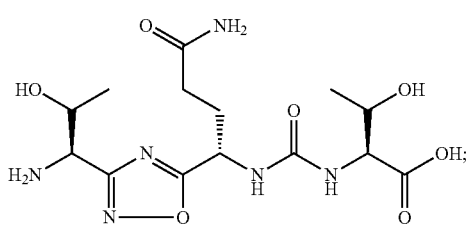 [SMILES: CC(O)[C@H](NC(=O)N[C@@H](CCC(N)=O)c1nc([C@@H](N)C(C)O)no1)C(=O)O]

or a pharmaceutically acceptable salt thereof.

45. The method according to claim 1, wherein the compound has the following structure:

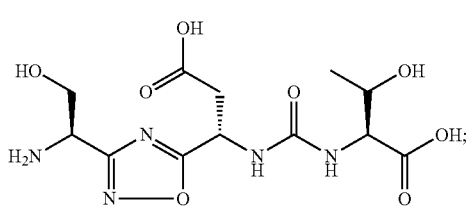 [SMILES: CC(O)[C@H](NC(=O)N[C@@H](CC(=O)O)c1nc([C@@H](N)CO)no1)C(=O)O]

or a pharmaceutically acceptable salt thereof.

46. The method according to claim 15, wherein the compound has the following structure:

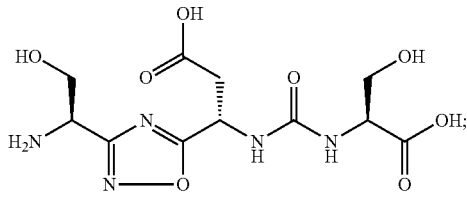 [SMILES: N[C@@H](CO)c1noc([C@H](CC(=O)O)NC(=O)N[C@@H](CO)C(=O)O)n1]

or a pharmaceutically acceptable salt thereof.

47. The method according to claim 1, wherein the cancer is selected from the group consisting of breast cancer, colon cancer, lung cancer, melanoma, prostate cancer, and renal cancer.

48. The method according to claim 47, wherein the cancer is bone cancer, cancer of the head or neck, pancreatic cancer, skin cancer, cutaneous or intraocular malignant melanoma, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, and combinations of said cancers.

* * * * *